United States Patent [19]
Eliash et al.

[11] Patent Number: 5,296,124
[45] Date of Patent: Mar. 22, 1994

[54] METHOD OF IN-SITU FORMATION OF A STABLE REFERENCE ELECTRODE FOR IN-TANK PLATING BATH ANALYSIS

[75] Inventors: Bruce M. Eliash, Los Angeles; Vilambi N. R. K. Reddy, Lakewood; Frank A. Ludwig, Rancho Palos Verdes; Nguyet H. Phan, Los Angeles, all of Calif.

[73] Assignee: Hughes Aircraft Company, Los Angeles, Calif.

[21] Appl. No.: 974,650

[22] Filed: Nov. 10, 1992

[51] Int. Cl.$^5$ ............................................. G01N 27/26
[52] U.S. Cl. ..................................... 204/402; 204/412; 204/434; 204/435; 204/153.1
[58] Field of Search ................. 204/DIG. 8, 412, 402, 204/434, 435, 153.1, DIG. 9; 205/103, 104, 105, 86

[56] References Cited

U.S. PATENT DOCUMENTS 2,951,978  5/1957  Dickson et al. ............... 204/DIG. 9
4,631,116 12/1986  Ludwig ............................. 204/434

OTHER PUBLICATIONS

Teach et al., Cyclic Pulse Voltammetric Stripping Analysis of Acid Copper Plating Baths, 1984, pp. 831-834.

*Primary Examiner*—John Niebling
*Assistant Examiner*—Bruce F. Bell
*Attorney, Agent, or Firm*—M. E. Lachman; M. W. Sales; W. K. Denson-Low

[57] ABSTRACT

A method of forming a reference electrode having a continuously stable reference voltage and particularly well-suited for use in an in-tank electrochemical sensor. The method utilizes an inert substrate and a counter electrode, both immersed in electroplating fluid. Current is passed between the inert substrate and the counter electrode to strip and subsequently replate the inert substrate, which then serves as the reference electrode. The steps of stripping and replating the reference electrode are periodically repeated to maintain the stability of the reference electrode voltage.

10 Claims, 2 Drawing Sheets

METHOD OF IN-SITU FORMATION OF A STABLE REFERENCE ELECTRODE FOR IN-TANK PLATING BATH ANALYSIS

BACKGROUND OF THE INVENTION

1. Field of the Invention

The present invention relates to a method of in-situ formation of a reference electrode for in-tank use in plating bath analysis. More particularly, the present invention relates to a method for repeatedly regenerating a reference electrode to provide long-term reference voltage stability without replacing the electrode. The stable reference electrode is of the type ideally required in in-tank sensors used to accurately measure and analyze the electrochemical properties of plating baths.

2. Description of Related Art

Plating bath analysis methods, such as the method disclosed in U.S. Pat. No. 4,631,116, and assigned to the present common assignee, typically use electrochemical sensors containing sensing electrodes and a reference electrode. The sensing electrodes usually include a working electrode and a counter electrode. All of the electrodes are in direct contact with the plating bath solution. The electrochemical properties of the plating bath solution are measured by applying ac and dc signals to the solution via the sensing electrodes and measuring the resultant response signals. The reference electrode plays an important role in the proper functioning of the sensor, since it provides a reference voltage upon which the various ac and dc signals are applied and controlled at the sensing electrode during measurement.

The reference voltage is a function of the particular type of plating bath, and reflects changes in the bath that are independent of the applied signals. Basing response signal measurements on this reference voltage permits accurate monitoring of a variety of important electrochemical properties. Absent the reference voltage, normal ground-referenced voltage variations for a given plating bath will interfere with the control and response signals, preventing robust and accurate electrochemical analysis.

Commercially available standard reference electrodes are not suitable for in-tank use and suffer from the following limitations: frequent and time consuming maintenance, contamination of the plating bath, fouling, unsatisfactory stability, or structural characteristics not readily compatible with in-tank sensor designs.

Alternatively, wire reference electrodes with material matching the plating bath have been suggested for use. U.S. Pat. No. 4,812,210 describes various reference electrodes of this type. The wire may also be formed from a base metal substrate suitably plated for a particular application. Usually, the base metal is the same metal as the plating application or a less expensive material.

The reference electrodes described above suffer from a number of defects which render them inadequate for in-tank applications. The reference electrodes require costly and time-consuming maintenance, since they frequently wear out and must be replaced. Moreover, the plating on a plated reference electrode deteriorates over time, and can eventually flake off and contaminate the bath. The flakes can also accumulate in an electrochemical sensor and thereby interfere with the operation of the working and counter electrodes.

Furthermore, the currently utilized reference electrodes exhibit a voltage instability which is unacceptable in the many plating bath applications which require continuous operation for periods of several weeks or more. For example, tests performed on a solid copper wire reference electrode showed that the electrode voltage became unstable in less than 24 hours. This type of voltage instability significantly degrades the accuracy and efficiency of voltammetric analysis techniques such as those described in U.S. Pat. No. 4,631,116. A user requiring continuous analysis of the plating bath must either accept continually degrading measurement accuracy or interrupt production to manually replace the reference electrodes several times a day.

As is apparent from the above, there presently is a need for a stable reference electrode for in-tank use which does not require replacement or generate contaminants within the plating bath or sensor. Further, the reference electrode should provide a stable voltage reference during the electrochemical analysis and over long periods of time. The reference electrode should provide these features and also be compatible with most in-tank electrochemical sensors, plating baths and the measurement methods and equipment associated therewith.

SUMMARY OF THE INVENTION

In accordance with the present invention a method is provided for forming a stable reference electrode. The reference electrode is particularly well-suited for use in an in-tank electrochemical sensor of the type used to monitor plating baths by ac and dc voltammetry.

The method involves providing an inert reference electrode substrate and a counter electrode, both of which are immersed in electroplating fluid. A sufficient current is passed between the inert substrate and counter electrode to remove previous layers of metal plating and other contaminants from the inert substrate and otherwise prepare the substrate for plating. An electroplating current is then passed between the inert substrate and the counter electrode in order to electrodeposit a fresh layer of metal on the cleaned and prepared inert substrate. The method thus quickly and efficiently forms the reference electrode by stripping and replating its inert substrate.

As a feature of the present invention, the reference electrode so formed is regenerated rather than replaced, essentially eliminating the maintenance time and expense associated with reference electrodes currently used. The inert reference electrode substrate is formed of a material able to withstand wear from repeated stripping and replating, and therefore rarely requires replacement.

In accordance with the present invention, the steps of completely stripping and then replating a new deposit each time prevents excessive material build-up and, thereby, eliminates problems associated with flaking of the reference electrode. The method of the present invention thus prevents the contamination of the plating bath and interference with sensor measurements associated with reference electrode flaking.

As an additional feature of the present invention, the reference electrodes so formed are readily adaptable for use within many different in-tank electrochemical sensors and measurement systems. The method of formation of the present invention thus eliminates the need for custom reference electrode design and can provide a standard reference electrode which is structurally compatible with most in-tank sensors.

As another feature of the present invention, the method may be used with a variety of different plating baths. An accurate and stable reference electrode can be formed as long as there is sufficient metallic content in the bath.

In accordance with the present invention the reference electrode formation method may be performed using the same equipment and instrumentation typically used with voltammetric plating bath analysis methods such as those disclosed in U.S. Pat. No. 4,631,116. The method of the present invention is thus easily integrated into known plating bath analysis techniques to further improve the flexibility and efficiency of an overall electrochemical monitoring system.

As a further feature of the present invention, the formation of the reference electrode is accomplished very rapidly so as to not unduly interfere with plating bath analysis. The newly deposited layer of metal plating exhibits a rapidly equilibrated metal-solution interface and it is thus possible to continue making accurate electrochemical measurements almost immediately after the reference electrode is regenerated.

The above-discussed features and attendant advantages of the present invention will become better understood by reference to the following detailed description of the preferred embodiments and the accompanying drawings.

DETAILED DESCRIPTION OF THE PREFERRED EMBODIMENT

Figure 1:
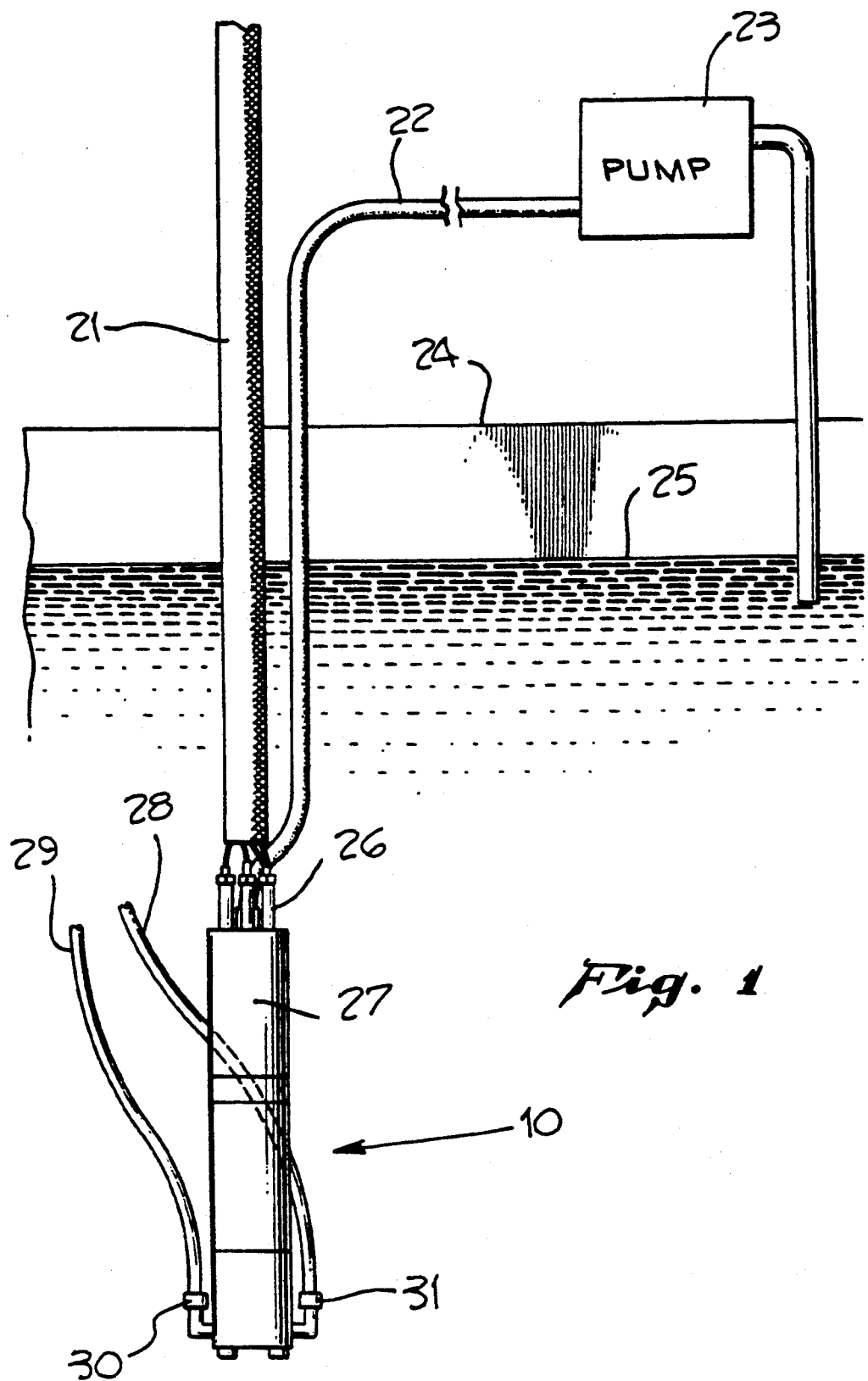
FIG. 1 is a side view of an exemplary in-tank electrochemical sensor incorporating a preferred embodiment of a reference electrode formed in accordance with the method of the present invention.

Exemplary electrochemical analysis methods and equipment, to which the method of forming a stable reference electrode of the present invention is applied, are described in U.S. Pat. No. 4,631,116, which has been previously discussed. The contents of this patent are hereby expressly incorporated by reference. The application of plating bath analysis methods such as those described in U.S. Pat. No. 4,631,116, for in-tank use are made possible through the in-situ formation of a reference electrode which yields stable voltages during the electrochemical measurements and over substantial periods of time.

The method of the present invention uses an inert material, preferably formed of platinum or gold as the substrate of the reference electrode. A counter electrode also made of inert material is required to provide, in conjunction with the inert substrate, a path for current to be applied for stripping and plating the inert substrate. The substrate and counter electrodes are both submerged in electroplating solution. The electroplating solution comprises metals which are capable of being electroplated, including, but not limited to, copper, iron, nickel, chromium, zinc, gold, silver, lead, platinum, cadmium, palladium, rhodium, indium, cobalt, tin and mixtures therefor.

First, any residual plated material or other contaminants on the inert substrate are stripped away via the application of sufficient current between the substrate and counter electrode. This current is preferably a constant DC current with a current density of about 100 to 1000 milliamperes per square centimeter, but other current waveforms may be suitable as well. Among the contaminants on the inert substrate which are removed in this step are plating from previous electrode formation, adsorbed organics, and adsorbed inorganics. The application of a high level of constant current insures complete removal of all contaminants. The current is applied until substantially all of the contaminants are removed from the substrate. The time required for this will vary depending upon a variety of parameters. In general, application of the current for between about 10 and 60 seconds is sufficient. The current is applied from an external source, which may be the same source as that used for the sensor which is described below.

After the substrate has been cleaned and prepared, current is again applied to electrodeposit a layer of metal plating on the substrate. A preferred current waveform is a pulsed waveform with a current density of about 50 to 300 milliamperes per square centimeter, a period of about 1 to 10 seconds and a pulse duration of about 100 to 1000 milliseconds. It should be noted that any suitable electroplating current waveform can be used in this step, including constant current waveforms. The metal plating can be copper or any other metal suitable for the given application.

By way of example, the invention is described for an acid copper plating bath application. First, a constant anodic current density of 750 milliamperes per square centimeter is applied to an inert platinum substrate for a period of 20 seconds. This current serves to strip off any copper from the previous formation procedure, oxidize any adsorbed organic material on the platinum substrate, and generally prepare the substrate for the next step of electrodeposition.

Next, a pulsed current waveform with a peak current density of about 250 milliamperes per square centimeter, a period of about 1 second, and a pulse duration of about 100 milliseconds is used to electrodeposit a layer of copper on the platinum substrate. The resultant reference electrode reaches about 98 percent of its final steady state voltage within about 10 to 20 seconds. Although other electroplating waveforms could be used for acid copper plating baths, the pulsed current waveform was found to yield reference electrodes with better voltage stability.

A summary of data obtained for seven reference electrode formation trials is presented in Table 1. The reference electrode so formed maintains a very stable voltage with a drift of less than or equal to 0.4 mv/min. The reformed electrodes provide open circuit voltages that vary about ±2 mv. Therefore, numerous highly accurate electrochemical measurements can be performed before reforming the reference electrode.

TABLE 1.

| Trial | Summary of reference electrode formation trials | |
|---|---|---|
| | Electrode Voltage (mv vs. SCE) | Voltage Drift (mv/min) |
| 1 | 60 | 0.38 |
| 2 | 63 | 0.36 |
| 3 | 63 | 0.4 |
| 4 | 58.6 | 0.38 |
| 5 | 59.7 | 0.36 |

TABLE 1.-continued

Summary of reference electrode formation trials

| Trial | Electrode Voltage (mv vs. SCE) | Voltage Drift (mv/min) |
|---|---|---|
| 6 | 59.2 | 0.36 |
| 7 | 59.5 | 0.32 |

Figure 2:
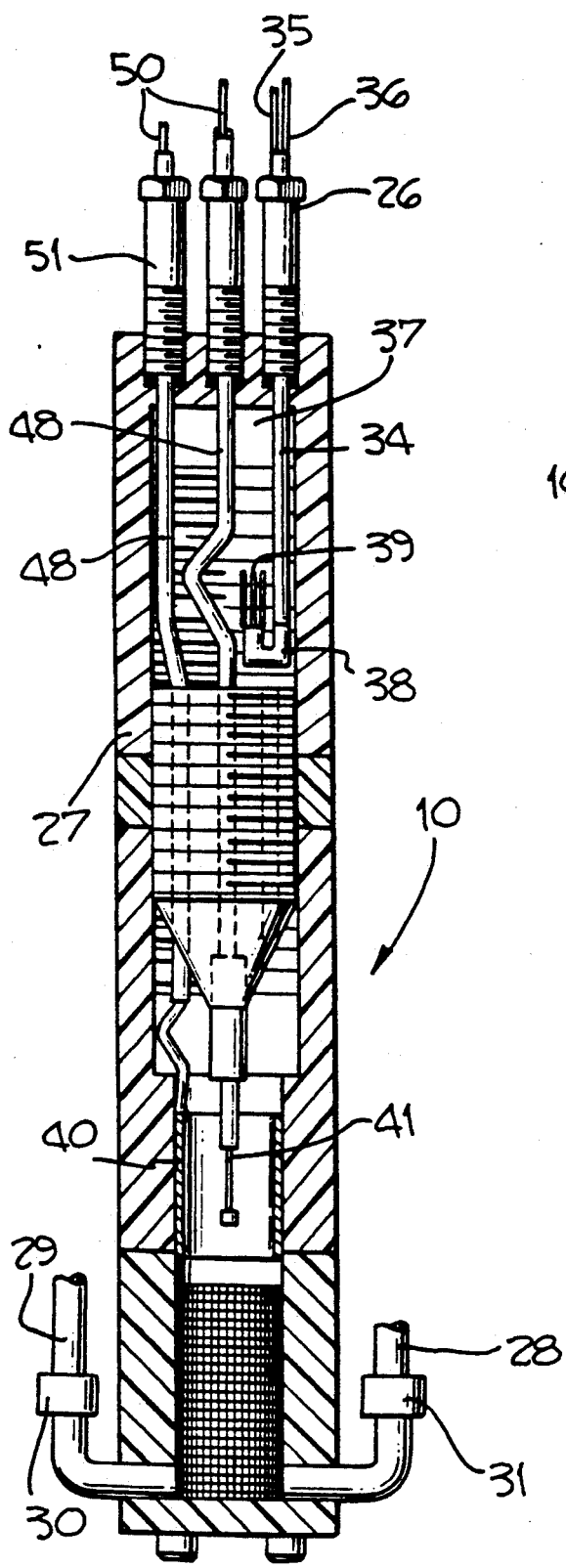
FIG. 2 is a side sectional view of the exemplary electrochemical sensor of FIG. 1 showing the location of the reference electrode within the sensor.

FIGS. 1 and 2 show a side view of an exemplary in-tank electrochemical sensor 10 suitable for use with the method of the present invention and the plating bath analysis techniques described in U.S. Pat. No. 4,631,116. The sensor 10 is immersed in a plating tank 24 filled with electroplating liquid 25. The liquid 25 flows through the sensor 10 via a pump 23 and tubing 22. The pump 23 draws the liquid 25 into the sensor 10 through inlet tubes 28, 29 and inlets 30, 31. The liquid then passes through the sensor 10 and pump 23 and back into the tank 24. Counter electrode 40 and working electrode 41 serve as sensing electrodes for electrochemical measurement. In traveling through the sensor 10, the liquid passes sensing electrodes 40, 41 and finally a reference electrode 39. The sensing electrodes 40, 41 are powered and monitored via wires 50 which enter the sensor through bushings 51 and are protected by shielding 48. All sensing electrode measurements are taken relative to the reference voltage supplied by the reference electrode 39.

The exemplary reference electrode 39 is connected to an external current generating and control apparatus via wires 35, 36 which enter into the sensor 10 via leak-proof bushing 26. Electrode wires 35, 36, 50 are supported and protected by shielding tube 21 as they exit the plating tank 24. The reference electrode 39 is preferably located within the interior 37 of the fluid exit chamber 27 of sensor 10 above sensing electrodes 40, 41. However, reference electrode 39 can be located elsewhere in the sensor 10.

Figure 3:
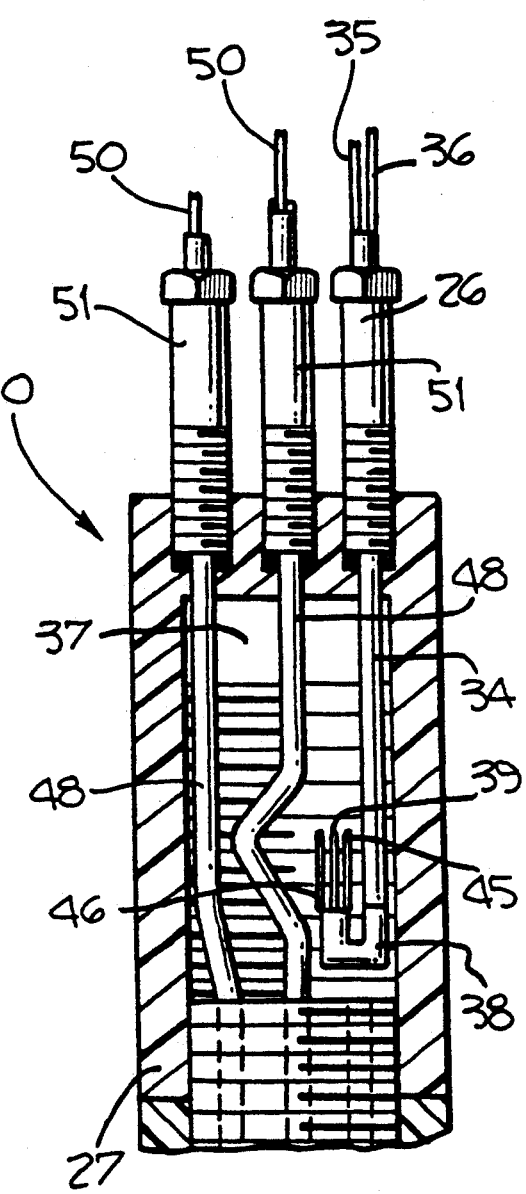
FIG. 3 is a detailed side sectional view of the reference electrode installed within the sensor of FIG. 1.

FIG. 3 shows exemplary reference electrode 39 in greater detail. In the preferred embodiment shown, the reference electrode 39 is formed on an inert platinum substrate extending upward from a securing base 38 and surrounded by two counter electrodes 45, 46. An appropriate current is passed between the reference electrode 39 and counter electrodes 45, 46 via wires 35, 36 entering the sensor 10 through leak-proof bushing 26. One of the wires 35, 36 is in electrical contact with the inert substrate while the other is in electrical contact with the counter electrodes 45, 46. Both wires 35, 36 are conveyed to their respective electrodes under shielding 34. The counter electrodes 45, 46 are preferably in close proximity to the reference electrode. All electrodes are immersed within the electroplating liquid 25 which passes through the sensor 10 during electrochemical analysis.

The shape and location of the reference and counter electrodes shown in FIG. 3 are exemplary only and many alternative shapes, locations, and arrangements of these elements are possible. For example, electrodes 45, 46 could serve as inert substrates upon which reference electrodes are formed and electrode 39 could then serve as a counter electrode.

Although the above description has been limited to reference electrodes for use within in-tank electrochemical sensors used for plating bath analysis, this is by way of illustration and not limitation. For example, the method described herein could also be useful in many other plated electrode applications. It will be understood by those skilled in the art that many alternate implementations of this method are possible without deviating from the scope of the invention, which is limited only by the appended claims.

I claim:

1. A method for forming a reference electrode having a stable reference voltage and adapted for use in an in-tank electrochemical sensor, said method comprising the steps of:
   providing at least one inert substrate;
   providing at least one counter electrode;
   providing a liquid containing a metal which is electroplated onto said inert substrate;
   passing a level of current between said inert substrate and said counter electrode for a time to thereby remove contaminants which are present on said inert substrate to provide a stripped inert substrate wherein said current applied to remove contaminants from said inert substrate is a current waveform with a current density of about 100 to 1000 milliamperes per square centimeter; and
   passing a level of current between said stripped inert substrate and said counter electrode for a time to electrodeposit a layer of said metal from said liquid onto said stripped inert substrate to form said reference electrode.

2. The method of claim 1 wherein said steps of passing said level of current to remove contaminants and passing said level of current to electrodeposit a layer of metal are repeated periodically to thereby provide a reference electrode with a consistently stable reference voltage during electrochemical measurements and over long periods of time.

3. The method of claim 1 wherein said liquid is an electroplating liquid which contains said metal.

4. The method of claim 1 wherein said inert substrate is formed from a metal selected from the group consisting of platinum and gold.

5. The method of claim 1 wherein said current applied to remove contaminants from said inert substrate is a constant current waveform applied continuously for a period of about 10 to 60 seconds.

6. The method of claim 1 wherein said current applied to electrodeposit a layer of metal on said substrate is a current waveform with a current density of about 5 to 300 milliamperes per square centimeter.

7. The method of claim 1 wherein said current applied to electrodeposit a layer of metal on said inert substrate is a periodic current waveform with a period of about 1 to 10 seconds.

8. The method of claim 1 wherein said current applied to electrodeposit a layer of metal on said inert substrate is a pulsed current waveform with a pulse duration of about 100 to 1000 milliseconds.

9. The method of claim 1 wherein said reference voltage reaches about 98 percent of its steady-state voltage value about 10 to 20 seconds after the formation of said reference electrode.

10. The method of claim 3 wherein said electroplating liquid includes a metal selected from the group consisting of copper, iron, nickel, chromium, zinc, tin, gold, silver, lead, platinum, cadmium, palladium, rhodium, indium, cobalt and mixtures thereof.

* * * * *